(12) United States Patent
Bernard et al.

(10) Patent No.: US 10,478,322 B2
(45) Date of Patent: Nov. 19, 2019

(54) RETRACTOR DEVICE FOR TRANSFORMING A RETRIEVAL DEVICE FROM A DEPLOYED POSITION TO A DELIVERY POSITION

(71) Applicant: Covidien LP, Mansfield, MA (US)

(72) Inventors: Francis Bernard, Dana Point, CA (US); Kenneth Brown, Oceanside, CA (US)

(73) Assignee: Covidien LP, Mansfield, MA (US)

( * ) Notice: Subject to any disclaimer, the term of this patent is extended or adjusted under 35 U.S.C. 154(b) by 292 days.

(21) Appl. No.: 15/626,265

(22) Filed: Jun. 19, 2017

(65) Prior Publication Data

US 2018/0360629 A1    Dec. 20, 2018

(51) Int. Cl.
| | | |
|---|---|---|
| *A61F 2/90* | (2013.01) | |
| *A61B 17/12* | (2006.01) | |
| *A61B 17/221* | (2006.01) | |
| *A61B 17/00* | (2006.01) | |
| *A61B 17/34* | (2006.01) | |

(52) U.S. Cl.
CPC .......... *A61F 2/90* (2013.01); *A61B 17/12118* (2013.01); *A61B 17/221* (2013.01); *A61B 2017/00469* (2013.01); *A61B 2017/2212* (2013.01); *A61B 2017/2215* (2013.01); *A61B 2017/3435* (2013.01)

(58) Field of Classification Search
CPC ... A61F 2/90; A61B 17/12118; A61B 17/221; A61B 2017/3435; A61B 2017/2215; A61B 2017/00469; A61B 2017/2212
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Dormia |
| 3,996,938 A | 12/1976 | Clark, III |
| 4,347,846 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |
| 4,790,812 A | 12/1988 | Hawkins, Jr. et al. |
| 4,807,626 A | 2/1989 | McGirr |

(Continued)

FOREIGN PATENT DOCUMENTS

| | | |
|---|---|---|
| CN | 1640505 A | 7/2005 |
| CN | 102036611 A | 4/2011 |

(Continued)

*Primary Examiner* — Phong Son H Dang
(74) *Attorney, Agent, or Firm* — Fortem IP LLP; Vijay Kumar

(57) ABSTRACT

Devices and methods for transforming a covered retrieval device from a deployed position to a delivery position for re-use are disclose herein. A retractor device may include, for example, a tubular structure defining a channel and configured to slidably receive a retrieval device. A method for transforming a retrieval device may include, for example, (a) positioning a retrieval device in a deployed position within a channel of a retractor device, (b) securing a part of the cover against a surface of the retractor, and (c) while securing the cover, advancing the retrieval device distally through the tubular structure to expose a capture structure of the retrieval device.

10 Claims, 11 Drawing Sheets

(56) References Cited

U.S. PATENT DOCUMENTS

| | | |
|---|---|---|
| 4,832,055 A | 5/1989 | Palestrant |
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1* | 4/2001 | Dubrul .............. A61B 17/221 600/159 |
| 6,238,412 B1* | 5/2001 | Dubrul ............... A61B 17/22 606/108 |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1* | 8/2003 | Mazzocchi ...... A61B 17/12022 606/200 |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,399,308 B2 | 7/2008 | Borillo et al. |
| 7,404,820 B2* | 7/2008 | Mazzocchi ...... A61B 17/12022 604/90 |
| 7,534,252 B2 | 5/2009 | Sepetka et al. |
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 8,603,014 B2 | 12/2013 | Alleman et al. |

(56) References Cited

U.S. PATENT DOCUMENTS

| | | | |
|---|---|---|---|
| 8,795,305 B2* | 8/2014 | Martin | A61F 2/06 606/159 |
| 8,837,800 B1 | 9/2014 | Bammer et al. | |
| 8,932,319 B2* | 1/2015 | Martin | A61F 2/06 606/200 |
| 9,119,656 B2 | 9/2015 | Bose et al. | |
| 9,126,018 B1 | 9/2015 | Garrison | |
| 9,211,132 B2 | 12/2015 | Bowman | |
| 9,241,699 B1 | 1/2016 | Kume et al. | |
| 9,254,371 B2* | 2/2016 | Martin | A61B 17/221 |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,427,244 B2* | 8/2016 | Lund-Clausen | A61B 17/221 |
| 9,445,828 B2 | 9/2016 | Turjman et al. | |
| 9,445,829 B2 | 9/2016 | Brady et al. | |
| 9,463,036 B2* | 10/2016 | Brady | A61B 17/221 |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,717,519 B2* | 8/2017 | Rosenbluth | A61B 17/32072 |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,833,252 B2* | 12/2017 | Sepetka | A61B 17/221 |
| 9,861,783 B2 | 1/2018 | Garrison et al. | |
| 9,962,178 B2* | 5/2018 | Greenhalgh | A61M 25/0119 |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 10,327,883 B2* | 6/2019 | Yachia | A61F 2/013 |
| 2001/0041909 A1 | 11/2001 | Tsugita et al. | |
| 2001/0044632 A1 | 11/2001 | Daniel et al. | |
| 2001/0044634 A1 | 11/2001 | Don Michael et al. | |
| 2001/0051810 A1* | 12/2001 | Dubrul | A61B 17/221 606/159 |
| 2002/0002396 A1 | 1/2002 | Fulkerson | |
| 2002/0004667 A1 | 1/2002 | Adams et al. | |
| 2002/0026211 A1 | 2/2002 | Khosravi et al. | |
| 2002/0058904 A1 | 5/2002 | Boock et al. | |
| 2002/0062135 A1 | 5/2002 | Mazzocchi et al. | |
| 2002/0072764 A1 | 6/2002 | Sepetka et al. | |
| 2002/0072765 A1* | 6/2002 | Mazzocchi | A61B 17/12022 606/200 |
| 2002/0082558 A1 | 6/2002 | Samson et al. | |
| 2002/0123765 A1 | 9/2002 | Sepetka et al. | |
| 2002/0138094 A1 | 9/2002 | Borillo et al. | |
| 2002/0151928 A1 | 10/2002 | Leslie et al. | |
| 2002/0169474 A1 | 11/2002 | Kusleika et al. | |
| 2002/0188314 A1 | 12/2002 | Anderson et al. | |
| 2002/0193825 A1 | 12/2002 | McGuckin et al. | |
| 2003/0004542 A1 | 1/2003 | Wensel et al. | |
| 2003/0023265 A1 | 1/2003 | Forber | |
| 2003/0040771 A1 | 2/2003 | Hyodoh et al. | |
| 2003/0050663 A1 | 3/2003 | Khachin et al. | |
| 2003/0060782 A1 | 3/2003 | Bose et al. | |
| 2003/0093087 A1 | 5/2003 | Jones et al. | |
| 2003/0144687 A1 | 7/2003 | Brady et al. | |
| 2003/0153935 A1 | 8/2003 | Mialhe | |
| 2003/0176884 A1* | 9/2003 | Berrada | A61F 2/013 606/200 |
| 2003/0195556 A1 | 10/2003 | Stack et al. | |
| 2004/0068288 A1 | 4/2004 | Palmer et al. | |
| 2004/0073243 A1* | 4/2004 | Sepetka | A61B 17/22031 606/159 |
| 2004/0079429 A1 | 4/2004 | Miller et al. | |
| 2004/0133232 A1 | 7/2004 | Rosenbluth et al. | |
| 2004/0138692 A1 | 7/2004 | Phung et al. | |
| 2004/0153025 A1 | 8/2004 | Seifert et al. | |
| 2004/0153118 A1 | 8/2004 | Clubb et al. | |
| 2004/0172056 A1 | 9/2004 | Guterman et al. | |
| 2004/0199201 A1 | 10/2004 | Kellett et al. | |
| 2004/0199243 A1 | 10/2004 | Yodfat | |
| 2004/0210116 A1 | 10/2004 | Nakao | |
| 2004/0267301 A1 | 12/2004 | Boylan et al. | |
| 2005/0004594 A1 | 1/2005 | Nool et al. | |
| 2005/0033348 A1 | 2/2005 | Sepetka et al. | |
| 2005/0038447 A1 | 2/2005 | Huffmaster | |
| 2005/0043680 A1 | 2/2005 | Segal et al. | |
| 2005/0043756 A1 | 2/2005 | Lavelle et al. | |
| 2005/0049619 A1 | 3/2005 | Sepetka et al. | |
| 2005/0055033 A1 | 3/2005 | Leslie et al. | |
| 2005/0055047 A1 | 3/2005 | Greenhalgh | |
| 2005/0059995 A1 | 3/2005 | Sepetka et al. | |
| 2005/0080356 A1 | 4/2005 | Dapolito et al. | |
| 2005/0085826 A1 | 4/2005 | Nair et al. | |
| 2005/0085847 A1 | 4/2005 | Galdonik et al. | |
| 2005/0085849 A1 | 4/2005 | Sepetka et al. | |
| 2005/0090857 A1 | 4/2005 | Kusleika et al. | |
| 2005/0090858 A1 | 4/2005 | Pavlovic | |
| 2005/0125024 A1 | 6/2005 | Sepetka et al. | |
| 2005/0131450 A1 | 6/2005 | Nicholson et al. | |
| 2005/0171566 A1 | 8/2005 | Kanamaru | |
| 2005/0203571 A1 | 9/2005 | Mazzocchi et al. | |
| 2005/0209609 A1 | 9/2005 | Wallace | |
| 2005/0216030 A1 | 9/2005 | Sepetka et al. | |
| 2005/0216050 A1* | 9/2005 | Sepetka | A61B 17/22031 606/200 |
| 2005/0234501 A1 | 10/2005 | Barone | |
| 2005/0234505 A1 | 10/2005 | Diaz et al. | |
| 2005/0277978 A1 | 12/2005 | Greenhalgh | |
| 2005/0283166 A1 | 12/2005 | Greenhalgh | |
| 2005/0283186 A1 | 12/2005 | Berrada et al. | |
| 2006/0004404 A1 | 1/2006 | Khachin et al. | |
| 2006/0009784 A1 | 1/2006 | Behl et al. | |
| 2006/0030925 A1 | 2/2006 | Pryor | |
| 2006/0047286 A1 | 3/2006 | West | |
| 2006/0058638 A1 | 3/2006 | Bose et al. | |
| 2006/0058836 A1 | 3/2006 | Bose et al. | |
| 2006/0058837 A1 | 3/2006 | Bose et al. | |
| 2006/0095070 A1 | 5/2006 | Gilson et al. | |
| 2006/0129166 A1 | 6/2006 | Lavelle | |
| 2006/0129180 A1 | 6/2006 | Tsugita et al. | |
| 2006/0155305 A1 | 7/2006 | Freudenthal et al. | |
| 2006/0190070 A1 | 8/2006 | Dieck et al. | |
| 2006/0195137 A1 | 8/2006 | Sepetka et al. | |
| 2006/0229638 A1 | 10/2006 | Abrams et al. | |
| 2006/0253145 A1 | 11/2006 | Lucas | |
| 2006/0271153 A1 | 11/2006 | Garcia et al. | |
| 2006/0276805 A1 | 12/2006 | Yu | |
| 2006/0282111 A1 | 12/2006 | Morsi | |
| 2006/0287668 A1 | 12/2006 | Fawzi et al. | |
| 2007/0112374 A1* | 5/2007 | Paul, Jr. | A61F 2/013 606/200 |
| 2007/0118165 A1 | 5/2007 | DeMello et al. | |
| 2007/0149996 A1* | 6/2007 | Coughlin | A61F 2/013 606/200 |
| 2007/0185500 A1 | 8/2007 | Martin et al. | |
| 2007/0185501 A1 | 8/2007 | Martin et al. | |
| 2007/0197103 A1 | 8/2007 | Martin et al. | |
| 2007/0198029 A1 | 8/2007 | Martin et al. | |
| 2007/0198030 A1 | 8/2007 | Martin et al. | |
| 2007/0198051 A1 | 8/2007 | Clubb et al. | |
| 2007/0225749 A1 | 9/2007 | Martin et al. | |
| 2007/0233236 A1 | 10/2007 | Pryor | |
| 2007/0265656 A1 | 11/2007 | Amplatz et al. | |
| 2008/0109031 A1 | 5/2008 | Sepetka et al. | |
| 2008/0183198 A1 | 7/2008 | Sepetka et al. | |
| 2008/0188885 A1 | 8/2008 | Sepetka et al. | |
| 2008/0262528 A1 | 10/2008 | Martin | |
| 2008/0262532 A1 | 10/2008 | Martin | |
| 2009/0069828 A1 | 3/2009 | Martin et al. | |
| 2009/0105722 A1 | 4/2009 | Fulkerson et al. | |
| 2009/0105737 A1 | 4/2009 | Fulkerson et al. | |
| 2009/0125053 A1 | 5/2009 | Ferrera et al. | |
| 2009/0192518 A1 | 7/2009 | Golden et al. | |
| 2009/0287291 A1 | 11/2009 | Becking et al. | |
| 2009/0299393 A1 | 12/2009 | Martin et al. | |

(56) References Cited

U.S. PATENT DOCUMENTS

| | | |
|---|---|---|
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0268264 A1* | 10/2010 | Bonnette .............. A61B 17/221 606/200 |
| 2010/0318097 A1 | 12/2010 | Ferrera et al. |
| 2011/0015718 A1* | 1/2011 | Schreck .................. A61F 2/07 623/1.12 |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2013/0030461 A1 | 1/2013 | Marks et al. |
| 2013/0281788 A1 | 10/2013 | Garrison |
| 2013/0289589 A1* | 10/2013 | Krolik .................. A61B 17/221 606/159 |
| 2014/0276074 A1 | 9/2014 | Warner |
| 2014/0276403 A1* | 9/2014 | Follmer ............ A61B 17/22032 604/103.02 |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0354098 A1 | 12/2016 | Martin et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0259042 A1* | 9/2017 | Nguyen ............ A61B 17/22032 |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |
| 2018/0325531 A1* | 11/2018 | Skillrud .............. A61B 17/221 |
| 2018/0325532 A1* | 11/2018 | Skillrud .............. A61B 17/221 |
| 2018/0325534 A1* | 11/2018 | Skillrud .............. A61B 17/221 |
| 2018/0325535 A1* | 11/2018 | Skillrud .............. A61B 17/221 |
| 2018/0368863 A1* | 12/2018 | Skillrud .............. A61B 17/221 |
| 2019/0133628 A1* | 5/2019 | Follmer .......... A61B 17/22032 |

FOREIGN PATENT DOCUMENTS

| | | |
|---|---|---|
| DE | 3501707 A1 | 7/1986 |
| EP | 200668 A2 | 11/1986 |
| EP | 1312314 A1 | 5/2003 |
| EP | 2319575 B1 | 11/2013 |
| JP | 2002537943 A | 11/2002 |
| JP | 2007-522881 A | 8/2007 |
| JP | 2007252951 A | 10/2007 |
| JP | 2011508635 | 3/2011 |
| JP | 2014004219 A | 1/2014 |
| JP | 2018118132 A | 8/2018 |
| KR | 20180102877 A | 9/2018 |
| WO | WO-94/09845 A1 | 5/1994 |
| WO | WO-95/09586 A1 | 4/1995 |
| WO | WO-9601591 A1 | 1/1996 |
| WO | WO-96/17632 A2 | 6/1996 |
| WO | WO-96/19941 A1 | 7/1996 |
| WO | WO-97/27808 A1 | 8/1997 |
| WO | WO-97/27893 A1 | 8/1997 |
| WO | WO-98/03120 A1 | 1/1998 |
| WO | WO-00/53120 A1 | 9/2000 |
| WO | WO-0072909 A1 | 12/2000 |
| WO | WO-01/32254 A1 | 5/2001 |
| WO | WO-01/54622 A1 | 8/2001 |
| WO | WO-01/67967 A1 | 9/2001 |
| WO | WO-02/02162 | 1/2002 |
| WO | WO-02/28291 A2 | 4/2002 |
| WO | WO-03/000334 A1 | 1/2003 |
| WO | WO-03/061730 A2 | 7/2003 |
| WO | WO-03/089039 A1 | 10/2003 |
| WO | WO-2006/031410 A2 | 3/2006 |
| WO | WO-2006/122076 A1 | 11/2006 |
| WO | WO-2007092820 A2 | 8/2007 |
| WO | WO-2008/036156 A1 | 3/2008 |
| WO | WO-2008036156 | 3/2008 |
| WO | WO-2008/131116 A1 | 10/2008 |
| WO | 2008539958 A | 11/2008 |
| WO | WO-2009/034456 A2 | 3/2009 |
| WO | WO-2009/086482 A1 | 7/2009 |
| WO | WO-2011/091383 A1 | 7/2011 |
| WO | WO-2011091383 | 7/2011 |
| WO | WO-2012009675 A2 | 1/2012 |
| WO | WO-2012/162437 A1 | 11/2012 |
| WO | WO-2013/106146 A1 | 7/2013 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

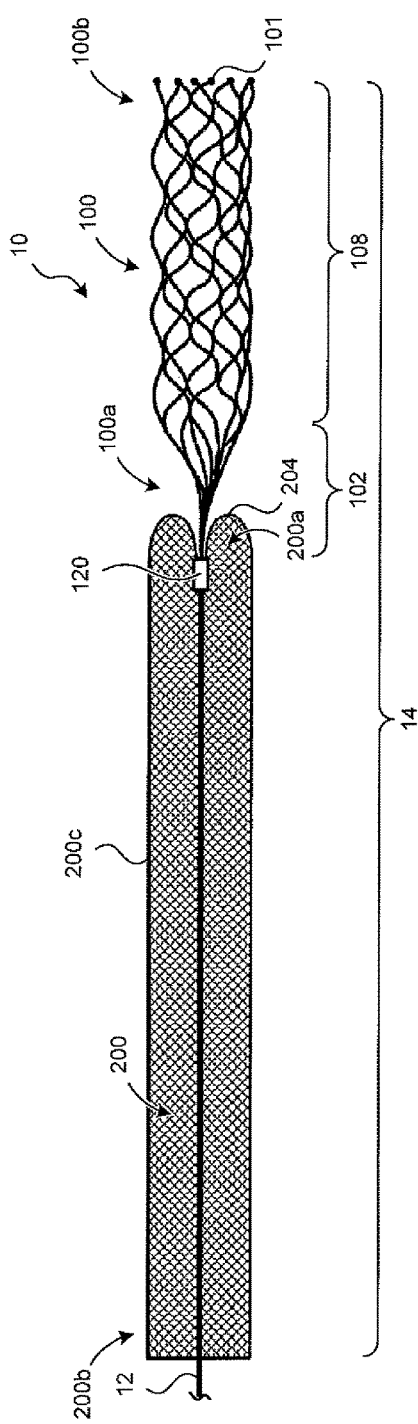
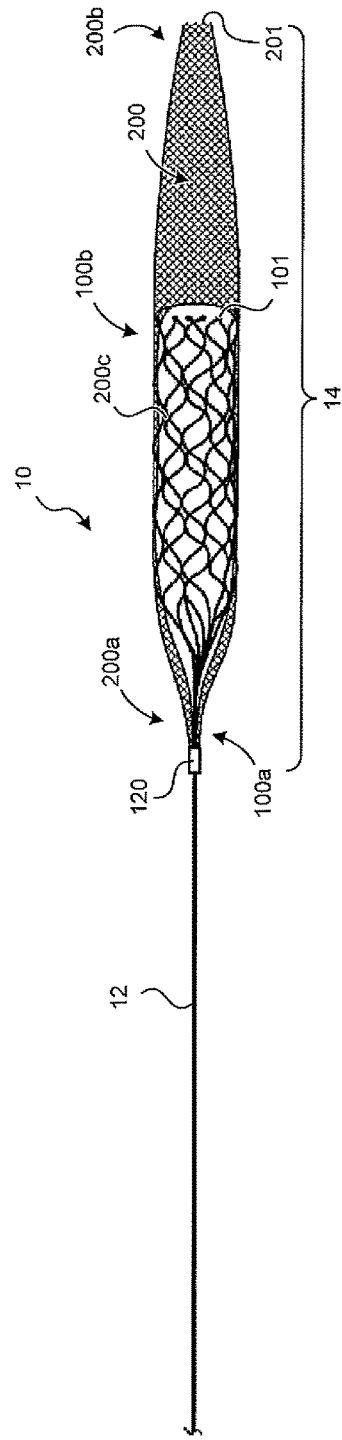
FIG. 1A
FIG. 1B

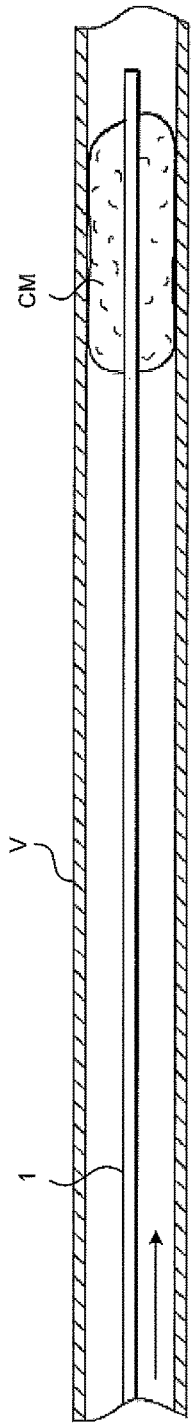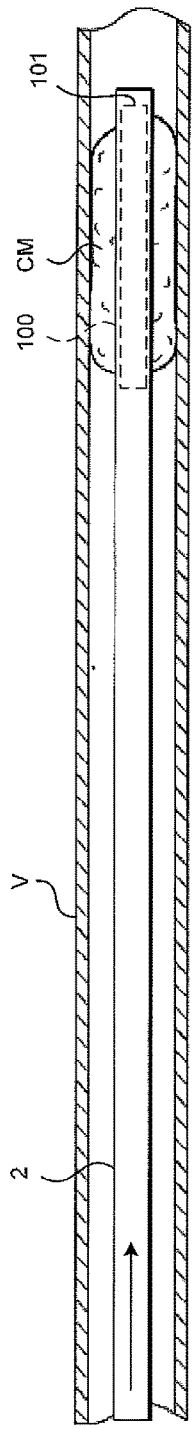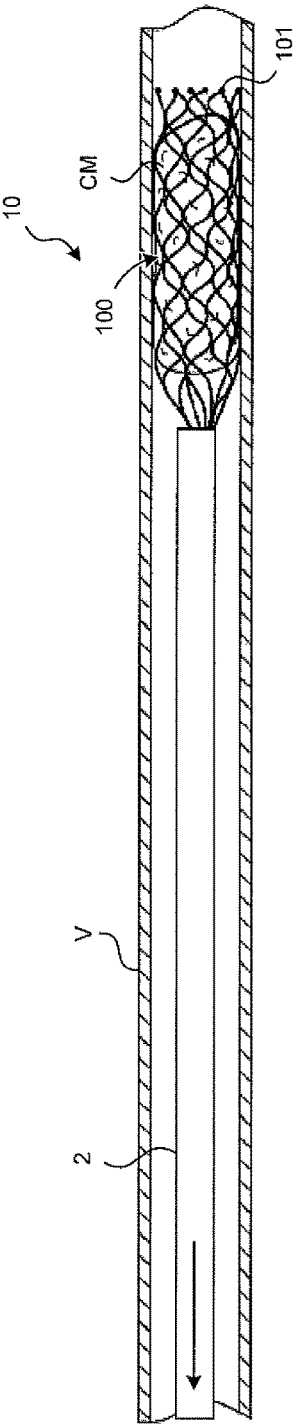

RETRACTOR DEVICE FOR TRANSFORMING A RETRIEVAL DEVICE FROM A DEPLOYED POSITION TO A DELIVERY POSITION

TECHNICAL FIELD

The present technology relates generally to devices and methods for removing obstructions from body lumens. Some embodiments of the present technology relate to removing clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Even in successful procedures, a physician must be cautious to prevent the walls of the vessel or body lumen from imparting undesired forces to shear or dislodge the obstruction as it passes through the vasculature during removal. These forces have the potential of fragmenting the obstruction. In some cases, the obstruction can simply break free from the retrieval device and can lodge in a new area causing more concern than the original blockage.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death (infarction). Accordingly, it is desirable to provide immediate medical treatment of an ischemic stroke. To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and is easy for the physician to perform, there remain some distinct disadvantages to using this approach.

For example, one disadvantage is that the stent may not sufficiently retain the clot as it pulls the clot to the catheter. In such a case, some or all of the clot might remain within the vasculature. Another risk is that as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, since the stent is oversized compared to the vessel, dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels.

SUMMARY

At least some of the embodiments disclosed herein involves devices, systems, and methods for retrieving clot material from a blood vessel lumen. For example, some embodiments are directed to a retrieval device (such as a clot retrieval device) that includes an elongated shaft configured to be intravascularly positioned at or adjacent clot material within a blood vessel lumen, and a retrieval assembly coupled to a distal region of the elongated shaft. The retrieval assembly may include a flexible cover and a capture structure. The retrieval assembly may be deployed within the blood vessel lumen at or near the clot material such that the capture structure engages or otherwise becomes enmeshed with at least a portion of the clot material, and at least a portion of the cover presses outward against the blood vessel wall proximal of the capture structure. Pulling the elongated shaft proximally everts the cover over the capture structure such that the cover at least partially ensheathes the capture structure and associated clot material. The retrieval assembly can then be withdrawn to remove the retrieval device and associated clot material from the patient.

In at least some embodiments of the present technology, a retractor device can be used to transform the retrieval device from a deployed position to a delivery position for re-use. In the deployed position, the cover at least partially ensheathes the capture structure. In the delivery position, the cover ensheathes less of the capture than in the deployed position (e.g., ensheathes no portion of the capture structure). In some embodiments, the retractor can have a tubular structure configured to slidably receive the retrieval device. The tubular structure can have a length no greater than twice the length of the capture structure.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 11, or clause 20. The other clauses can be presented in a similar manner.

1. A kit for retrieving material (e.g. luminal obstructive material such as clot) from a body of a subject, the kit comprising:
    a retrieval device including an elongated shaft and a retrieval assembly coupled to a distal zone of the elongated shaft, wherein—
        the retrieval assembly includes a capture structure and a cover,
        the cover has a first portion coupled to the distal zone of the elongated shaft and a free second portion, and
        the cover has a first position in which the second portion extends proximally from the first portion, a second position in which the second portion extends distally from the first portion, and the cover surrounds at least a portion of the capture structure in the second position; and
    a retractor having a tubular structure that defines a channel configured to slidably receive the retrieval device, wherein the tubular structure has a length no greater than twice the length of the capture structure measured along a longitudinal axis, and wherein the retractor is configured to extend distally beyond the capture structure to facilitate moving the cover from the second position after deployment to the first position for redeployment.
2. The kit of clause 1 wherein the retractor includes a longitudinal slot extending the entire length of the tubular structure, and wherein the slot has a width at least as great as the outer diameter of the elongated shaft such that the elongated shaft can pass laterally through the slot and into the channel.
3. The kit of clause 1 wherein the channel further includes a stop sized to allow the elongated shaft to pass through the stop and to inhibit proximal movement of the retrieval assembly when the elongated shaft is pulled proximally.
4. The kit of clause 1 wherein the retractor includes a longitudinal slot extending the entire length of the tubular structure and onto a proximal portion of the tubular structure, wherein the slot has a width at least as great as the outer diameter of the elongated shaft such that the elongated shaft can pass laterally through the slot and into the channel, and wherein the proximal portion of the tubular structure is configured to inhibit proximal movement of the retrieval assembly when the elongated shaft is pulled proximally.
5. The kit of clause 1 wherein at least one of the capture structure and the cover is a mesh.
6. The kit of clause 1 wherein the capture structure is a stent and the cover is a braid.
7. The kit of clause 1 wherein the length of the capture structure is greater than the length of the tubular structure.
8. The kit of clause 1 wherein the device further includes a handle configured to be gripped by a user when the cover is moved from the second position to the first position for redeployment.
9. The kit of clause 8 wherein the handle is coupled to the tubular structure nearer to a proximal portion of the tubular structure than a distal portion of the tubular structure.
10. The kit of clause 2 wherein the device further includes a handle having a planar shape and coupled to the tubular structure such that the handle is perpendicular relative to a plane extending through the longitudinal slot.
11. A method comprising:
    positioning at least a portion of a retrieval assembly of a retrieval device within a channel defined by a retractor such that least a distal terminus of a capture structure of the retrieval assembly is within the channel, wherein the retrieval assembly is coupled to an elongated shaft, and wherein the retrieval assembly is in a deployed configuration in which a cover of the retrieval assembly extends distally relative to the capture structure and surrounds at least a portion of the capture structure;
    securing part of the cover against an outer surface of the retractor; and
    while securing the part of the cover, advancing the retrieval assembly distally through the channel such that at least the distal terminus of the capture structure extends distally from the retractor and the cover.
12. The method of clause 11 wherein securing comprises securing the part of the cover against an outer surface of the retractor.
13. The method of clause 11 wherein securing comprises securing part of the cover against an outer surface of the retractor while another part of the cover is located in the channel, between an outer surface of the capture structure and an inner wall of the channel.
14. The method of clause 11, further comprising:
    removing the retrieval assembly from the retractor when the retrieval assembly is in a delivery position in which the cover extends proximally relative to the capture structure.
15. The method of clause 11, further comprising:
    manipulating a distal portion of the cover onto the retractor, wherein manipulating the cover includes everting a portion of the cover.
16. The method of clause 11 wherein advancing the retrieval assembly further includes exposing a distal portion of the capture structure and advancing the retrieval assembly distally by pulling distally on the exposed portion of the capture structure.
17. The method of clause 11 wherein advancing the retrieval assembly includes pushing the elongated shaft distally and/or pushing the retrieval assembly distally.
18. The method of clause 11, further comprising:
    before positioning the portion of the retrieval assembly, positioning the elongated shaft within the channel of the retractor.
19. The method of clause 18 wherein positioning the portion of the retrieval assembly further includes pulling the elongated shaft proximally such that the retrieval assembly slides through the channel until the distal terminus of the capture structure is within the channel.
20. A retractor for transforming a retrieval device, comprising:

a tubular structure that defines a channel and having a distal portion, a proximal portion, and a length extending between the distal portion and the proximal portion, wherein— the channel is configured to slidably receive the retrieval device, the retrieval device including an elongated shaft coupled to a retrieval assembly having a capture structure and a cover, a retention surface of the retractor outside of the channel is configured to engage a portion of the cover and be held by one hand of an operator while at least a distal terminus of the capture structure is positioned within the channel such that the capture structure can be advanced through the channel while the cover remains in a secured position relative to the retractor, and a longitudinal slot extends the entire length of the tubular structure and has a width at least as great as the outer diameter of the elongated shaft such that the elongated shaft can pass laterally through the slot and into the channel; and a handle attached to the tubular structure configured to be held by another hand of the operator to hold the retractor while transforming the retrieval device.

21. The retractor of clause 20 wherein the channel further includes a stop sized to allow the elongated shaft to pass through the stop and to inhibit proximal movement of the retrieval assembly when the elongated shaft is pulled proximally.

22. The retractor of clause 20 wherein the longitudinal slot extends onto the proximal portion of the tubular structure and wherein the proximal portion is configured to inhibit proximal movement of the retrieval assembly when the elongated shaft is pulled proximally.

23. The retractor of clause 20 wherein the longitudinal slot extends through a sidewall of the tubular structure 24. The retractor of clause 20, further comprising a handle projecting from the tubular structure.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are explanatory and are intended to provide examples and further explanation of the subject technology as claimed.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A is a side view of a distal portion of a clot retrieval device shown with a retrieval assembly in a first configuration in accordance with the present technology.

FIG. 1B is a side view of the distal portion of the clot retrieval device of FIG. 1A, shown with the retrieval assembly shown in a second, everted configuration.

FIGS. 2A-2G illustrate a method of removing clot material from a blood vessel lumen using the clot retrieval device shown in FIGS. 1A and 1B.

DETAILED DESCRIPTION

Figure 2D:
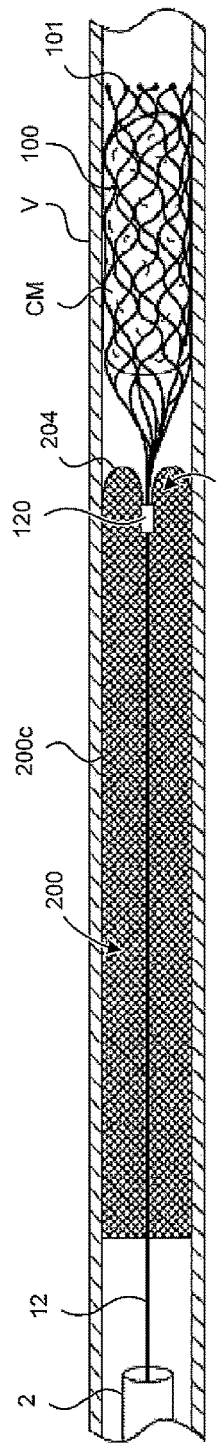

The present technology provides devices, systems, and methods for removing clot material from a blood vessel lumen. Although many of the embodiments are described below with respect to devices, systems, and methods for treating an ischemic stroke or cerebral embolism, other applications and other embodiments in addition to those described herein are within the scope of the technology. For example, the retrieval devices of the present technology may be used to remove emboli or other material from body lumens other than blood vessels (e.g., the digestive tract, etc.) and/or may be used to remove emboli from blood vessels outside of the brain (e.g., pulmonary blood vessels, blood vessels within the legs, etc.). In addition, the retrieval devices of the present technology may be used to remove luminal obstructions other than clot material (e.g., plaque, foreign bodies, resected tissue, etc.).

An overview of the retrieval devices of the present technology and associated methods of use is described below with reference to FIGS. 1A-2G. Particular embodiments of a retractor device according to the present technology and to be used with a retrieval device are described below with reference to FIGS. 3A-5G.

FIGS. 1A and 1B are side views of a distal portion of some embodiments of a retrieval device 10 ("device 10") outside of a blood vessel in an expanded, relaxed (e.g., unconstrained) configuration in accordance with the present technology. The retrieval device 10 is shown in first and second configurations in FIGS. 1A and 1B, respectively. As shown in FIGS. 1A and 1B, the retrieval device 10 includes an elongated shaft 12 ("shaft 12") and a retrieval assembly 14 coupled to a distal region of the elongated shaft 12 via a connection assembly 120. The retrieval assembly 14 is configured to be intravascularly positioned at or adjacent clot material (or other material to be retrieved such as plaques, foreign bodies, etc.) within a blood vessel lumen and includes a capture structure 100 and a flexible cover 200. In some embodiments, the capture structure 100 and the cover 200 are fixed to the elongated shaft 12 at generally the same location, or the capture structure 100 and cover 200 may be coupled to the shaft 12 at different locations and/or may be slidable with respect to the elongated shaft 12.

The capture structure 100 has a low-profile configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel. The capture structure 100 has a proximal portion 100a coupled to the shaft 12 and a distal portion 100b. The capture structure 100 further includes an open cell framework or body 108 (FIG. 1A) and a coupling region 102 (FIG. 1A) extending proximally from the body 108. In some embodiments, for example as shown in FIGS. 1A and 1B, a distal portion 100b of the capture structure 100 can be generally tubular (e.g., cylindrical), and the proximal portion 100a of the capture structure 100 tapers proximally to the coupling region 102. In some embodiments, the distal terminus of the distal portion 100b coincides with a distal terminus 101 of the capture structure 100 and/or retrieval assembly 14.

Referring again to FIGS. 1A and 1B, in some embodiments the capture structure 100 is a mesh structure formed of a superelastic material (e.g., Nitinol or other resilient or self-expanding material) configured to self-expand when released from the delivery catheter. For example, in some embodiments the capture structure 100 may be a stent and/or stentriever, such as Medtronic's Solitaire™ Revascularization Device, Stryker Neurovascular's Trevo® ProVue™ Stentriever, or other suitable devices. In other embodiments, the capture structure 100 may include a plurality of braided filaments. Examples of suitable capture structures 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The cover 200 includes a first end portion 200a coupled to the shaft 12 via the connection assembly 120, a free second end portion 200b, and a cover wall 200c extending between the first end portion 200a and the second end portion 200b. As used herein to describe the second end portion 200b of the cover 200, the term "free" refers to a portion of the cover 200 that is not fixed to the elongated shaft 12 and may move radially and/or longitudinally with respect to the shaft 12. The cover 200 is flexible such that it is movable between a first position (FIG. 1A) in which the free second end portion 200b is proximal of the first end portion 200a and a second position (FIG. 1B) in which the cover 200 is inverted over the capture structure 100 such that a distal terminus 201 (FIG. 1B) of the cover 200 is at or distal to the distal terminus 101 of the capture structure 100 and/or to the first end portion 200a. As shown in FIG. 1A, when the cover 200 is in the first position in an expanded, relaxed state, some embodiments of the cover 200 may have a leading edge 204 that overlaps the coupling region 102 of the capture structure 100 but does not extend beyond the coupling region 102 to overlap the body 108 of the capture structure 100. In some embodiments, the leading edge 204 of the cover 200 may also overlap all or a portion of the length of the body 108 when the cover 200 is in the first position. As shown in FIG. 1B, when the cover 200 is in the second position, the free second end portion 200b is distal of the first end portion 200a and distal of the distal terminus 101 of the capture structure 100. As such, when in the second position, the cover wall 200c surrounds the capture structure 100.

The cover 200 can comprise a mesh and/or braid of a plurality of wires (e.g., filaments, threads, sutures, fibers or the like) that have been interwoven to form a structure having openings (e.g., a porous fabric). The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In some embodiments, metal filaments may be highly polished and/or surface treated to further improve their hemocompatibility. The cover 200 can be constructed solely from metallic materials without the inclusion of any polymer materials, solely from polymer materials without the inclusion of any metallic materials, or a combination of polymer and metallic materials.

In some embodiments, some or all of the wires of the cover 200 are drawn-filled tube ("DFT") wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the cover 200 may have 72-144 total wires (e.g., 72, 96 128, 144, etc.) Moreover, some or all of the wires may have a wire diameter of about 0.005 inches to about 0.015 inches (e.g., 0.008 inches, 0.01 inches, etc.). In some embodiments, all of the wires have the same diameter, and in other embodiments some of the wires have different diameters.

FIGS. 2A-2G illustrate a method of removing clot material from the lumen of a blood vessel BV using the retrieval device 10 of the present technology. As shown in FIG. 2A, a guidewire 1 may be advanced through the clot material CM such that a distal terminus of the guidewire 1 is distal of the clot material CM. Next, a delivery catheter 2 may be delivered over the guidewire 1 so that a distal portion of the delivery catheter 2 is positioned at or near the clot material CM. As shown in FIG. 2B, in some embodiments the delivery catheter 2 may be advanced over the guidewire 1 through the clot material CM such that a distal terminus of the delivery catheter 2 is distal of the clot material CM. With the delivery catheter 2 in position, the guidewire 1 may be withdrawn. The retrieval device 10 may then be advanced through the delivery catheter 2 in a low-profile configuration until a distal terminus 101 of the capture structure 100 (shown schematically in FIG. 2B) is at or adjacent the distal terminus of the delivery catheter 2. As shown in FIGS. 2C and 2D, the delivery catheter 2 may then be pulled proximally relative to the retrieval device 10 to release the capture structure 100, thereby allowing the capture structure 100 to self-expand within the clot material CM. As the capture structure 100 expands, the capture structure 100 engages and/or secures the surrounding clot material CM, and in some embodiments may restore or improve blood flow through the clot material CM. In some embodiments, the capture structure 100 may be expanded distal of the clot material CM such that no portion of the capture structure 100 is engaging the clot material CM while the capture structure 100 is in the process of expanding toward the vessel wall. In some embodiments, the capture structure 100 is configured to expand into contact with the blood vessel wall, or the capture structure 100 may expand to a diameter that is less than that of the blood vessel lumen such that the capture structure 100 does not engage the entire circumference of the blood vessel wall.

As shown in FIG. 2D, the delivery catheter 2 may continue advancing proximally (as the user continues pulling it proximally) to release the cover 200 such that at least a portion of the cover wall 200c expands into contact with the blood vessel wall when the cover 200 is in the first position. Once the delivery catheter 2 is moved proximal of the cover 200 in the first position and both the cover 200 and the capture structure 100 are expanded within the vessel lumen, the retrieval assembly 14 is in the first configuration.

Figure 2E:
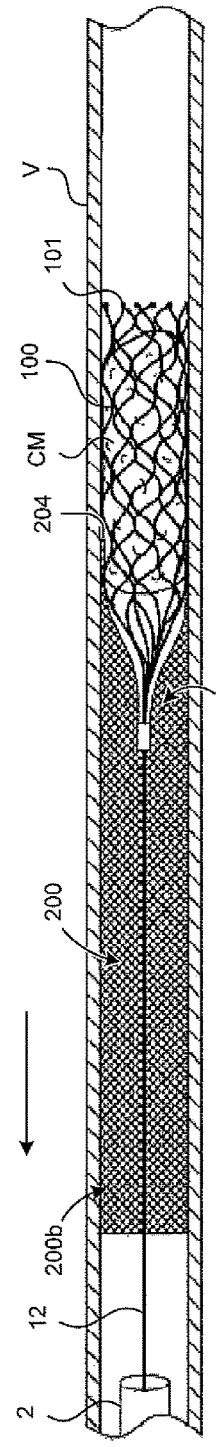
Figure 2F:
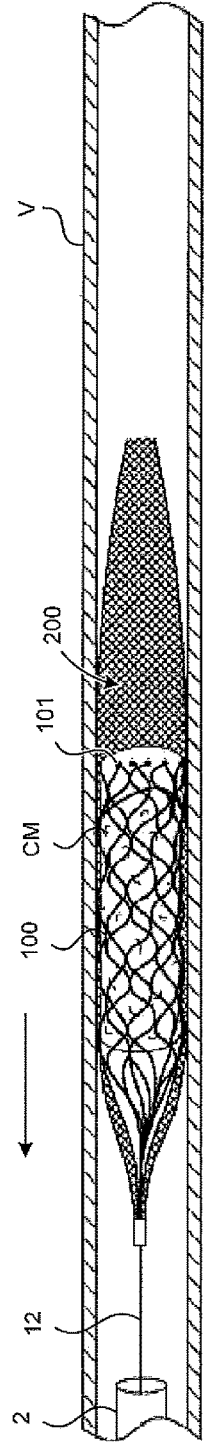
Figure 2G:
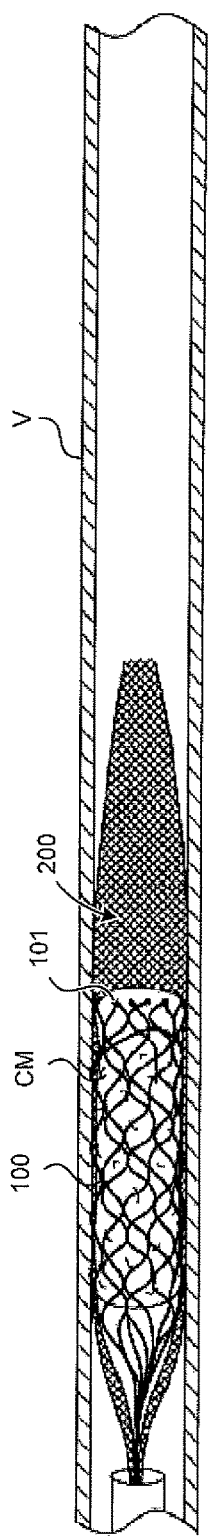

As shown in FIG. 2E, when the elongated shaft 12 is pulled proximally while the retrieval assembly 14 is in the first configuration, friction between the blood vessel wall and the cover wall 200c prevents or resists proximal movement of the free second end portion 200b of the cover 200 while the first end portion 200a of the cover 200 moves in a proximal direction with the capture structure 100. In other words, expansion of the cover 200 provides sufficient friction against the walls of the vessel V to overcome the column strength of the cover wall 200c, thereby causing the cover wall 200c to remain in place and/or move less than the first end portion 200a of the cover 200 so that the cover wall 200c inverts over the capture structure 100 and any associated clot material CM. As the elongated shaft 12 is moved proximally and the cover 200 is inverting, the capture structure 100 moves proximally relative to the leading edge 204 of the cover 200 so that the length of the capture structure 100 coextensive with the cover 200 increases. Eventually, the cover 200 completely inverts from the first position over the proximally advancing capture structure 100, thereby further securing any clot material held by or within the capture structure. As shown in FIG. 2G, the retrieval device 10 may continue advancing proximally (as the user continues pulling it proximally) until the retrieval assembly 14 is positioned within the delivery catheter 2. The delivery catheter 2, device 10, and associated clot material CM may then be withdrawn from the patient.

In some instances, the physician (i.e., a "user") using the retrieval device 10 may wish to re-use the retrieval device 10 after it has been delivered within a vessel. For example, the user may wish to re-use the retrieval device 10 in a second attempt to remove clot material CM from a vessel. However, once the clot retrieval assembly 14 is retracted proximally within the delivery catheter 2 (e.g., to remove the clot material CM), the cover 200 is in the second position (FIG. 1B). In some instances, the physician can manipulate the cover 200 from the second position to the first position (FIG. 1A) simply using their fingers. However, the cover 200 may rip, tear, or snag on the capture structure 100 when the physician attempts to move the cover 200 between the second and first positions. Moreover, such a process can slow down the overall process of redeploying the clot retrieval assembly 14.

FIGS. 3A-5G show various embodiments of retractors in accordance with the present technology for use with retrieval devices. The retractors discussed below are described with reference to the retrieval device 10 shown in FIGS. 1A-2G, but can be used in operation with any suitable covered retrieval device. A retractor according to the present technology is configured to move the cover 200 of retrieval device 10 from the second position (FIG. 1B) to the first position (FIG. 1A). As described above, in the first position, the free second end portion 200b of the cover 200 is proximal of the first end portion 200a and at least a portion of the capture structure 100 is exposed such that the cover 200 does not surround the capture structure 100. In the second position, the cover 200 is inverted over the capture structure 100 such that the free second end portion 200b of the cover 200 is distal of first end portion 200a and the cover 200 surrounds at least a portion of the capture structure 100. In some embodiments (e.g., as shown in FIG. 3B), the cover 200 can completely surround the capture structure 100 in the second position such that the distal terminus (i.e., absolute end) of the cover 200 is at or distal to the distal terminus 101 of the capture structure 100.

Figure 3A:
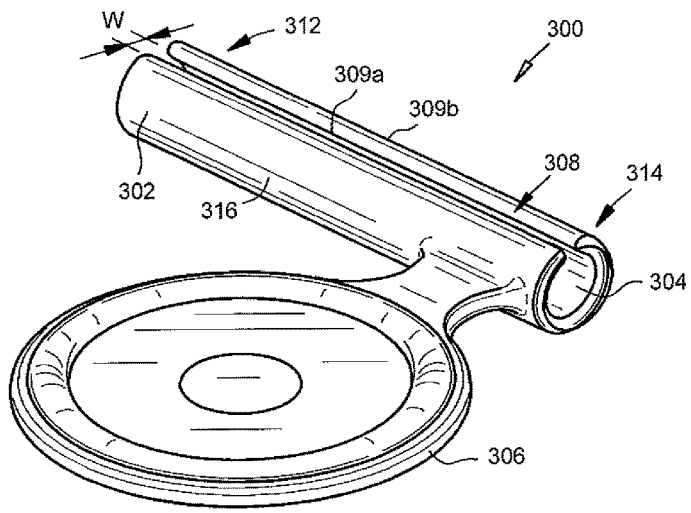
FIG. 3A is an isometric view of a retractor configured in accordance with the present technology.
Figure 3B:
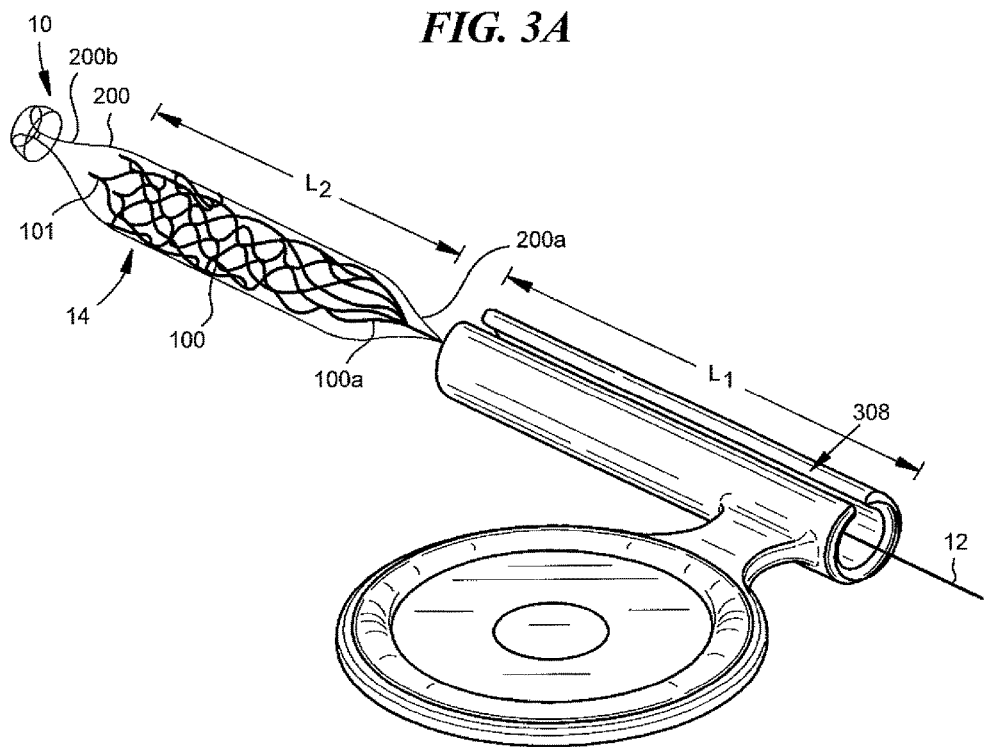
FIG. 3B is an isometric view of the retractor shown in FIG. 3A in operation with a retrieval device.

FIGS. 3A and 3B illustrate a retractor 300 in accordance with some embodiments of the present technology. The retractor 300 has a tubular structure 302 and a channel 304 extending longitudinally therethrough. Tubular structure 302 further includes a distal portion 312, a proximal portion 314, and an outside surface 316. As illustrated in FIG. 3B, the channel 304 is configured to slidably receive the retrieval device 10. In particular, the channel 304 has a diameter that is sized to slidably receive the elongated shaft 12 and the retrieval assembly 14 such that the retrieval device 10 can be pulled proximally or pushed distally through the tubular structure 302. The outside surface 316 of the tubular structure 302 is configured to engage a portion of the cover 200 for retracting the cover 200 proximally with respect to the retrieval assembly 14. As a result, the outside surface 316 can define a retention surface against which the cover 200 can be held.

As shown in FIG. 3B, the tubular structure 302 has a length $L_1$ extending between the distal portion 312 and the proximal portion 314. The capture structure 100 has a length $L_2$ measured along the same longitudinal axis as the length $L_1$. In some embodiments, the length $L_1$ of the tubular structure 302 is less than the length $L_2$ of the capture structure 100. In such embodiments, the proximal portion 100a of the capture structure 100 may protrude proximally from the proximal portion 314 of the tubular structure 302 when the retrieval assembly 14 is situated within the channel 304. In some embodiments, the length $L_1$ of the tubular structure 302 is greater than the length $L_2$ of the capture structure 100 such that the entire retrieval assembly 14, or the entire capture structure 100, may be contained within the tubular structure 302. However, the length $L_1$ of the tubular structure 302 is not more than twice the length $L_2$ of the capture structure 100.

In the embodiment illustrated in FIGS. 3A and 3B, the retractor 300 includes a slot 308 extending through the tubular structure 302 and longitudinally the entire length $L_1$ of the tubular structure 302. More specifically, the slot 308 can have edges 309a and 309b (collectively "edges 309") that extend along the length of the tubular structure 302. The slot 308 further has a width W between the edges 309 that is at least as great as an outer diameter of elongated shaft 12 such that the elongated shaft 12 can pass laterally through the slot 308 and into the channel 304. In some embodiments, the edges 309 can have a generally rounded or other shape without sharp or hard edges to avoid damaging the elongated shaft 12 when it passes through the slot 308. The slot 308 allows the retrieval device 10 to be positioned within the channel 304 without first threading the entire length of the elongated shaft 12 through the channel 304 of the retractor 300. Instead, a distal portion of the elongated shaft 12 can be passed laterally through slot 308. Once the elongated shaft 12 is within the channel 304, the elongated shaft 12 can then be pulled proximally, and/or the retractor 300 pushed distally, until the retrieval assembly 14 is positioned within the channel 304. In some embodiments, the tubular structure 302 does not include any slots and the channel 304 is fully enclosed.

The retractor 300 can further comprise a handle 306 extending from the tubular structure 302 and configured to be gripped by a user when the retractor 300 is used to move the cover 200 from the second position to the first position. The handle 306 can be coupled to the tubular structure 302 nearer to the proximal portion 314 of the tubular structure 302 than the distal portion 312. In some embodiments, the handle 306 has at least a generally planar shape and is coupled to the tubular structure 302 such that the handle 306 is perpendicular to a plane extending through the slot 308. In some embodiments, the handle 306 is attached at a different portion of the tubular structure 302 and can have a different shape or relative size. For example, the handle 306 can be a ring or other open shape that a user can grip.

The retractor 300 can be made out of a plastic or other materials. For example, in some embodiments, the retractor 300 is formed from high-density polyethylene ("HDPE"). Suitable materials can be injection molded, compression molded, or three-dimensionally printed into shape. Other well-known methods of manufacture can be used to form the retractor 300.

To move the cover 200 from the second position to the first position, the retrieval device 10 can be slidably disposed within the channel 304 such that the distal terminus 101 of the capture structure 100 is within channel 304. The cover 200 can then be secured against the outside surface 316 while the capture structure 100 is advanced distally through channel 304 to expose the capture structure 100. One advantage of using the retractor 300 is that the rigid external structure of the tubular structure 302 inhibits the cover 200 of the retrieval device from snagging on the capture structure 100 as the cover 200 moves from the second position to the first position. For example, without using the retractor 300, a user would need to grip either or both of the elongated shaft 12 and retrieval assembly 14 while attempting to manipulate the cover 200 from the second position to the first position. In doing so, without using the retractor 300, the distal terminus 101 of the capture structure 100 will frequently snag on the cover 200 when the cover 200 is moved proximally. This can increase the time required to prepare the retrieval device 10 for redeployment, and potentially damage the cover 200.

Figure 4A:
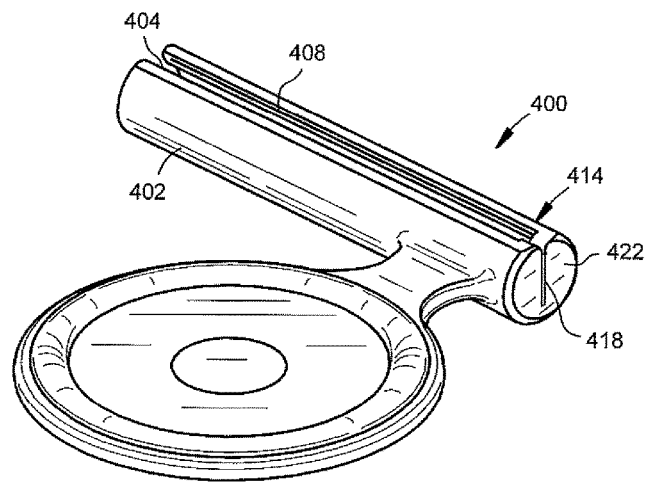
FIG. 4A is an isometric view of another embodiment of a retractor configured in accordance with the present technology.
Figure 4B:
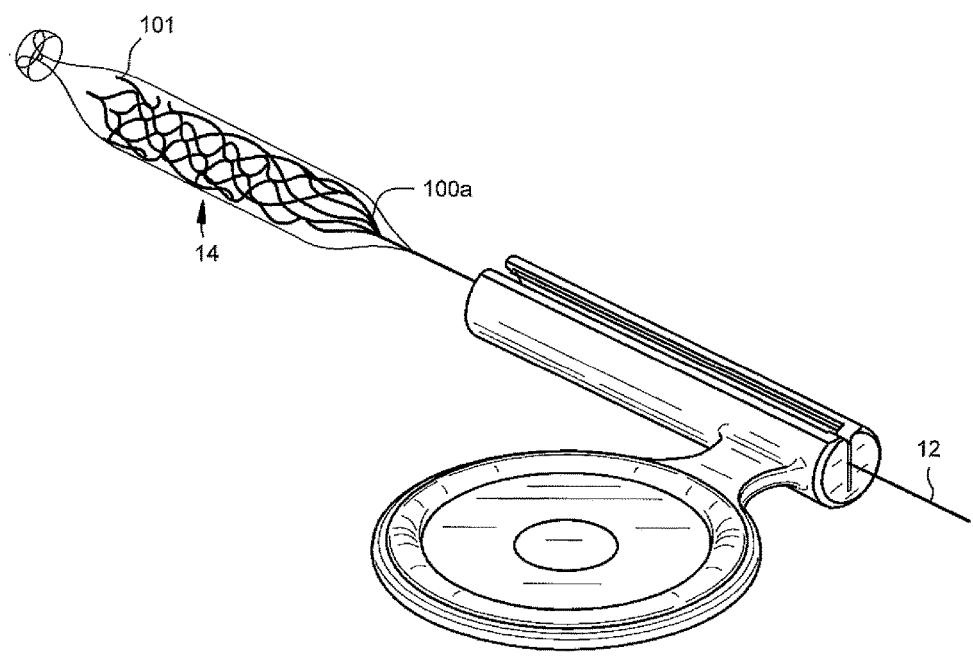
FIG. 4B is an isometric view of the retractor shown in FIG. 4A in operation with a retrieval device.
Figure 4C:
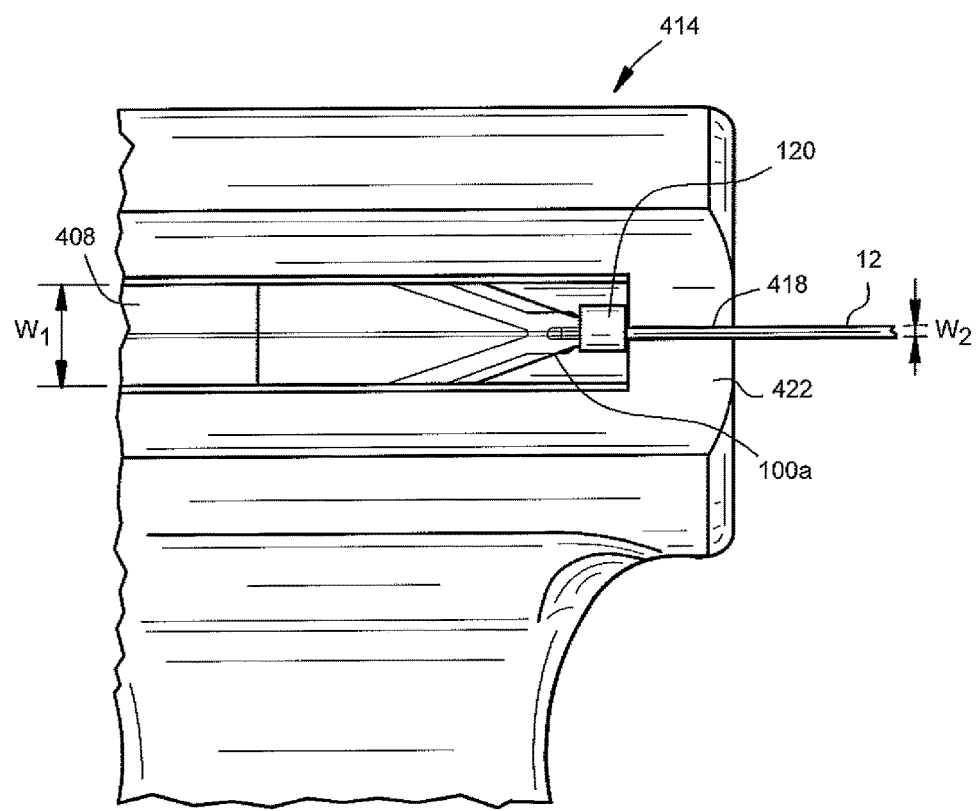
FIG. 4C is an enlarged side view of a proximal portion of the retractor in FIGS. 4A and 4B.

FIGS. 4A-4C show another embodiment of a retractor 400 configured in accordance with the present technology. FIGS. 4A and 4B illustrate a retractor 400 that includes some features generally similar to the features of the embodiment shown in FIGS. 3A and 3B. For example, retractor 400 includes a tubular structure 402 defining a channel 404, and a first slot 408 extending through and along the entire length of the tubular structure 402. The retractor 400 further includes a stop 422 having a slit 418 configured to receive the elongated shaft 12. The stop 422 limits proximal movement of the retrieval assembly 14.

In the embodiment shown in FIGS. 4A-4C, the slot 408 and the slit 418 combine to form a contiguous opening through the tubular structure 402 for receiving the elongated shaft 12. In some embodiments, the slit 418 has other shapes or configurations. For example, the slit 418 can be curved, L-shaped, or otherwise shaped to contain the elongated shaft 12 when it is moved through the stop 422.

FIG. 4C shows a side view of the proximal portion 414 of tubular structure 402. The slit 418 has a width $W_2$ that is at least as great as an outer diameter of the elongated shaft 12. This assures that the elongated shaft 12 can slide both distally and proximally through the slit 418. However, the width $W_2$ is smaller than an outer diameter of the proximal portion 100a of capture structure 100 and the connection assembly 120. Because the slit 418 is not sized to slidably receive either the capture structure 100 or the connection assembly 120, the stop 422 inhibits proximal movement of the retrieval assembly 14 when the elongated shaft 12 is pulled proximally. In the illustrated embodiment, the width $W_2$ of the slit 418 is less than a width $W_1$ of the slot 408. In some embodiments, the slot 408 and the slit 418 can have the same width, or the width $W_2$ of the slit 418 can be greater than the width $W_1$ of the slot 408.

The stop 422 defines a specific location within the retractor 400 for positioning the retrieval device 10. For example, the stop 422 can be located within the channel 404 such that when the retrieval assembly 14 engages the stop 422, the distal terminus 101 of the capture structure 100 is within the channel 404. The location of the stop 422 can also prevent the retrieval assembly 14 from being placed needlessly deep into the channel 404 and/or from sliding in the proximal direction out of the channel 404 during retraction of the cover 200. If placed too deep, more time and motion are required for manipulating the cover 200 onto the tubular structure 402. As illustrated in FIGS. 4A-4C, the stop 422 can be located at a proximal portion 414 of the tubular structure 402. In some embodiments, the stop 422 is located at a different position within the channel 404. For example, depending on the relative lengths of the capture structure 100 and tubular structure 402, the stop 422 can be positioned in a different location within the channel 404 (e.g., at a central portion or a distal portion of the channel 404) to serve as a locating feature for positioning the retrieval assembly 14.

Several aspects of methods for using the retractor 300 shown in FIGS. 3A and 3B to transform the cover 200 from the second position to the first position are shown in FIGS. 5A-5G. Some differences for using the retractor 400 (FIGS. 4A-4C) are described below, however, it is to be understood that the following method could generally be performed using a retractor according to any of the embodiments described herein. Moreover, in some figures, the user's fingers have been omitted so as not to obscure other features. Accordingly, even if not illustrated, the user may grip the handle 306 or other parts of the retractor 300 in order to carry out any or all of the steps described with reference to FIGS. 5A-5G.

Figure 5A:
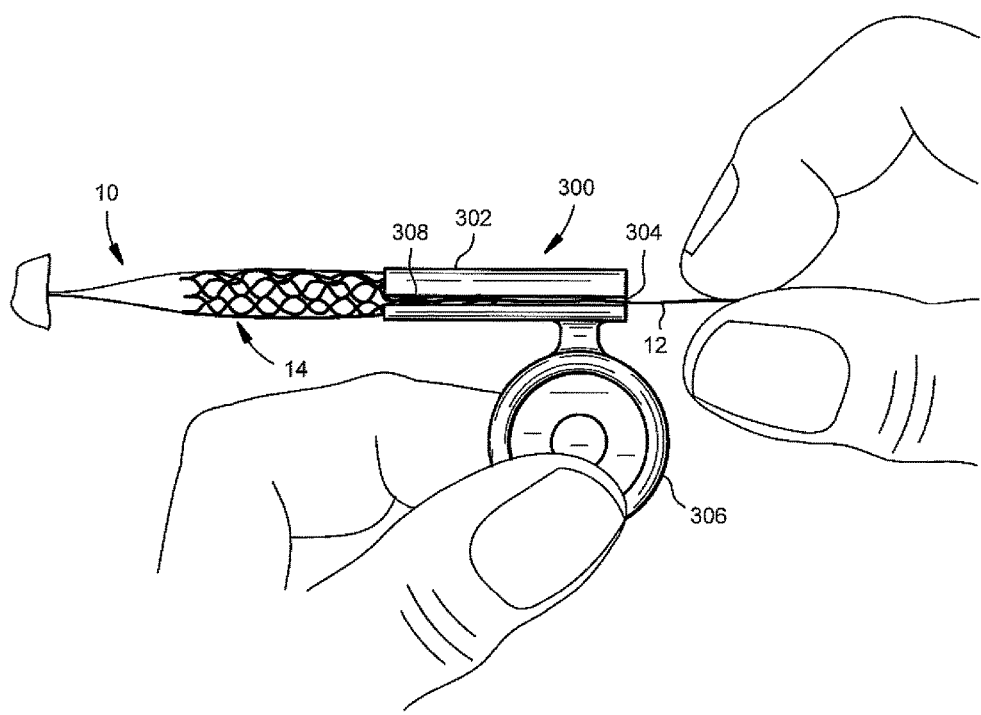
FIGS. 5A-5G illustrate a method of using a retractor in accordance with the present technology to facilitate the transformation of a retrieval device from a deployed configuration to a delivery configuration.

FIG. 5A illustrates the retrieval device 10 with the cover 200 in the second position and positioned partly within the channel 304 of the retractor 300. Before positioning the retrieval assembly 14 within channel 304, the elongated shaft 12 of the retrieval device 10 can be positioned within channel 304 as illustrated in FIG. 3B. For example, a distal portion of the elongated shaft 12 just proximal of the retrieval assembly 14 can pass laterally through the slot 308 and into the channel 304 of the tubular structure 302. The user can then pull proximally on the elongated shaft 12 such that the retrieval assembly 14 slides into and partly through the channel 304. More specifically, the user could grip the handle 306 with one hand while pulling proximally on the elongated shaft 12 to position the retrieval assembly 14 within the tubular structure 302. Alternatively or additionally, the retractor 300 can slide distally over the retrieval device 10 and/or the user can push/pull proximally on the retrieval assembly 14 to position the retrieval assembly 14 within the tubular structure 302 of the retractor 300.

Figure 5B:
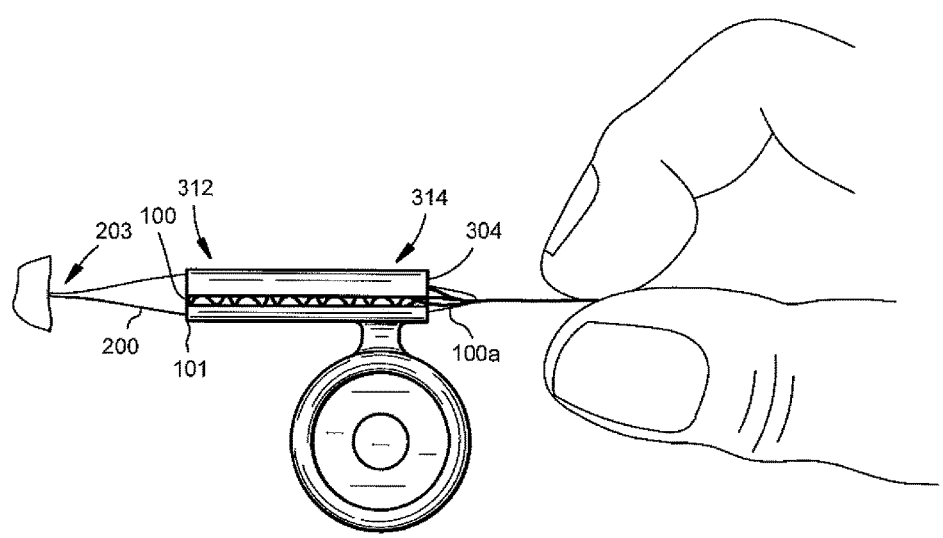

As illustrated in FIG. 5B, the retrieval device 10 is positioned within the retractor 300 such that the distal terminus 101 of the capture structure 100 is within the channel 304. This prevents the cover 200 from catching or snagging on the capture structure 100 when the cover 200 is later manipulated onto the tubular structure 302. In contrast to the embodiment illustrated in FIGS. 4A-4C, the user may need to visualize when the distal terminus 101 is within the retractor 300 without the stop 422 that locates the capture structure 100 at a specific location within the retractor 300.

Still referring to FIG. 5B, after the retrieval device 10 is positioned within the channel 304, a distal portion 203 (including the second end portion 200b) of the cover 200 extends distally from the distal portion 312 of the tubular structure 302 and remains outside of the channel 304. The distal portion 203 of the cover 200 remains outside of the channel 304 so that the cover 200 can later be manipulated onto the tubular structure 302. In some embodiments, depending on the relative lengths of the tubular structure 302 and the capture structure 100, a proximal portion 100a of the capture structure 100 may extend from the proximal portion 314 of the tubular structure 302 and outside of the channel 304. In some embodiments, such as the retractor 400, the capture structure 100 is positioned such that it is fully within the channel 404. As such, both the proximal portion 100a and the distal terminus 101 of the capture structure 100 can be within the channel in such cases.

Figure 5C:
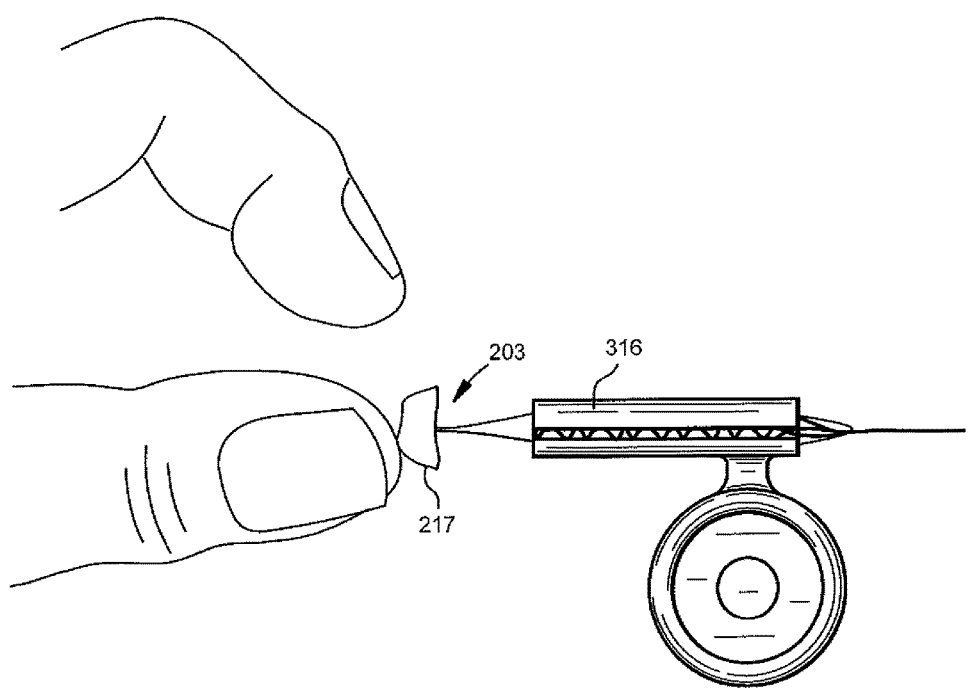
Figure 5D:
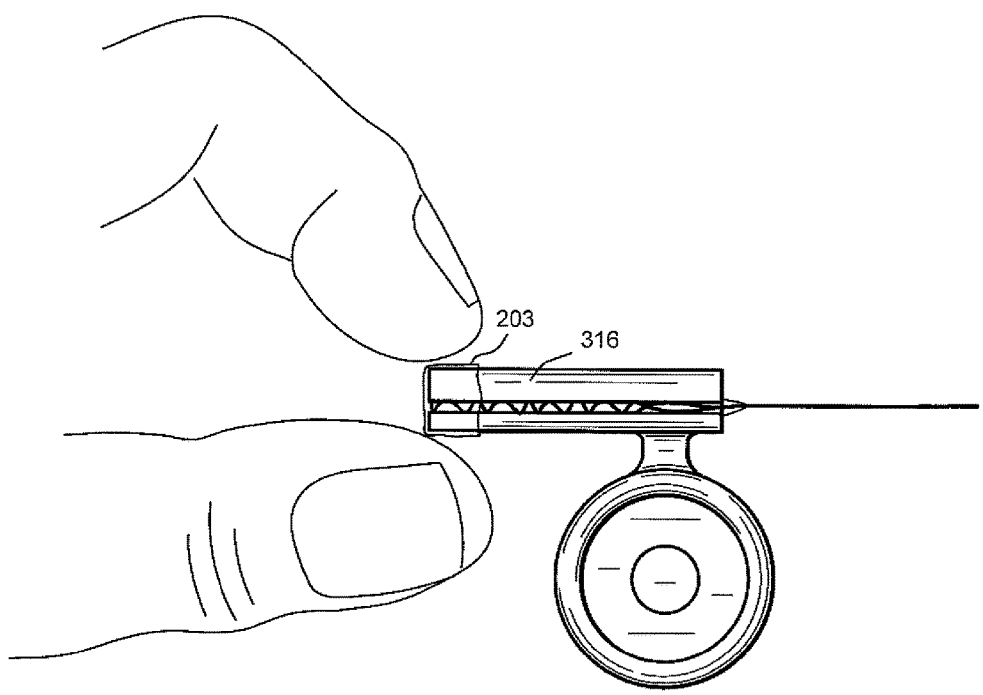

As shown in FIGS. 5C and 5D, once the retrieval device 10 is positioned within the retractor 300, the user can manipulate the distal portion 203 of the cover 200 onto the outside surface 316 of tubular structure 302. More specifically, the user can peel back the distal portion 203 of the cover 200 and push it onto the distal portion 312 of tubular structure 302 while the capture structure 100 is held stationary within the channel 304. As illustrated, the distal portion 203 of the cover 200 can have an end 217 that is everted relative to the rest of the cover 200 in the second position. In one embodiment, only this end 217 is manipulated onto the retractor 300. In some embodiments, the entire distal portion 203 of the cover 200 can be positioned around the outside surface 316 of the retractor 300. For example, FIG. 5E shows an embodiment in which a larger portion of the cover 200 than simply the end 217 has been manipulated onto the tubular structure 302.

Next, the cover 200 is secured against the outside surface 316 of the tubular structure 302. For example, the user can squeeze the portion of the cover 200 that is over the tubular structure 302 to clamp the cover 200 against the outside surface 316 of the tubular structure 302. In some embodiments, the cover 200 can be secured against the outside surface 316 of the tubular structure 302 by other mechanisms, such as a clamp or tie fastened around the portion of the cover on the outside surface 316.

Figure 5E:
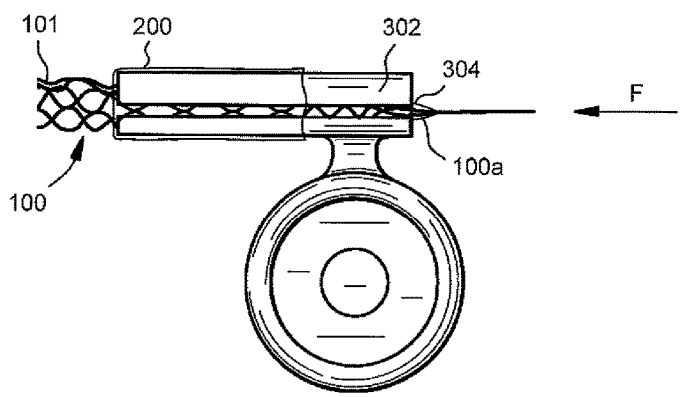

In a next step illustrated in FIG. 5E, the capture structure 100 is advanced distally through the retractor 300 while the cover 200 is pressed against the outer surface 316 such that at least the distal terminus 101 of the capture structure 100 extends distally from the tubular structure 302. Importantly, the distal terminus 101 of the capture structure 100 extends past the cover 200 such that the cover 200 no longer surrounds at least a portion of the capture structure 100. In some embodiments, the capture structure 100 is advanced distally through the channel 304 by applying a force in the distal direction to the elongated shaft 12 (indicated by arrow F in FIG. 5E) while the cover 200 is pressed against the outer surface 316. In some embodiments, where the proximal portion 100a of the capture structure 100 extends proximally outside the tubular structure 302, the capture structure 100 can be advanced by applying a force in the distal direction to the proximal portion 100a. For example, a user might push distally on the proximal portion 100a when the elongated shaft 12 is not configured to transmit sufficient column force to advance the capture structure 100 outside the retractor 300.

Figure 5F:
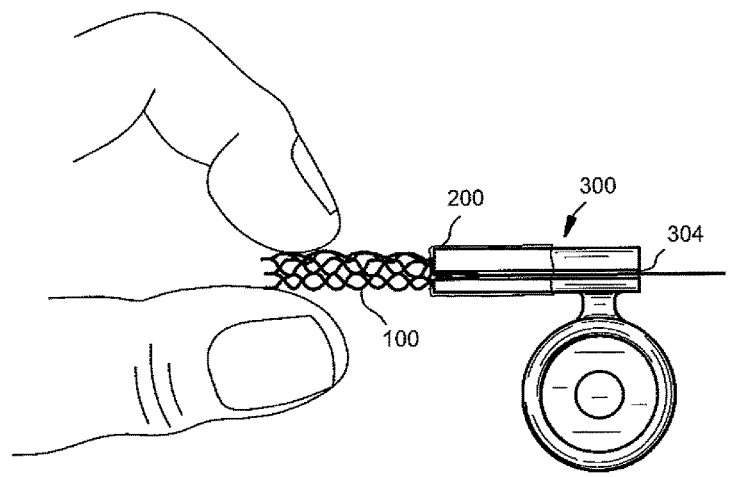

As shown in FIG. 5F, the user can then grip an exposed portion of the capture structure 100 and pull the capture structure 100 distally to further expose the capture structure 100 relative to the cover 200 and the retractor 300. Thus, the capture structure 100 can be advanced through the channel 304 by any combination of pushing distally on the elongated shaft 12 and/or pushing distally on the proximal portion 100a of the capture structure 100, and then by pulling distally on an exposed distal portion of the capture structure 100.

Figure 5G:
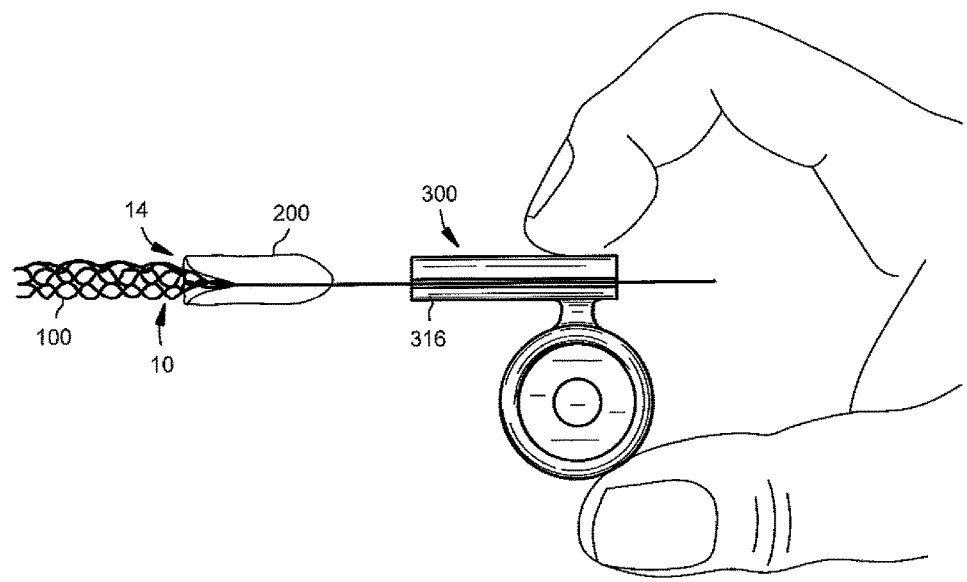

As illustrated in FIG. 5G, the cover 200 can be released from the outside surface 316 of the tubular structure 302 once the cover 200 is in the second position. In a final step, the retrieval device 10 is removed from the retractor 300. For example, the elongated shaft 12 may be removed from the channel 304 via the slot 308. The user can then clean and prepare the retrieval device for re-use.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with some embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A kit for retrieving material from a body of a subject, the kit comprising:
    a retrieval device including an elongated shaft and a retrieval assembly coupled to a distal zone of the elongated shaft, wherein—
        the retrieval assembly includes a capture structure and a cover, the cover has a first portion coupled to the distal zone of the elongated shaft and a free second portion, and the cover has a first position in which the second portion extends proximally from the first portion, a second position in which the second portion extends distally from the first portion, and the cover surrounds at least a portion of the capture structure in the second position; and a retractor having a tubular structure that defines a channel configured to slidably receive the retrieval device, wherein the tubular structure has a length no greater than twice a length of the capture structure measured along a longitudinal axis, and wherein the retractor is configured to extend distally beyond the capture structure to facilitate moving the cover from the second position after deployment to the first position for redeployment.

2. The kit of claim 1 wherein the retractor includes a longitudinal slot extending the entire length of the tubular structure, and wherein the slot has a width at least as great as the outer diameter of the elongated shaft such that the elongated shaft can pass laterally through the slot and into the channel.

3. The kit of claim 2 wherein the device further includes a handle having a planar shape and coupled to the tubular structure such that the handle is perpendicular relative to a plane extending through the longitudinal slot.

4. The kit of claim 1 wherein the channel further includes a stop sized to allow the elongated shaft to pass through the stop and to inhibit proximal movement of the retrieval assembly when the elongated shaft is pulled proximally.

5. The kit of claim 1 wherein the retractor includes a longitudinal slot extending the entire length of the tubular structure and onto a proximal portion of the tubular structure, wherein the slot has a width at least as great as the outer diameter of the elongated shaft such that the elongated shaft can pass laterally through the slot and into the channel, and wherein the proximal portion of the tubular structure is configured to inhibit proximal movement of the retrieval assembly when the elongated shaft is pulled proximally.

6. The kit of claim 1 wherein at least one of the capture structure and the cover is a mesh.

7. The kit of claim 1 wherein the capture structure is a stent and the cover is a braid.

8. The kit of claim 1 wherein the length of the capture structure is greater than the length of the tubular structure.

9. The kit of claim 1 wherein the device further includes a handle configured to be gripped by a user when the cover is moved from the second position to the first position for redeployment.

10. The kit of claim 9 wherein the handle is coupled to the tubular structure nearer to a proximal portion of the tubular structure than a distal portion of the tubular structure.

* * * * *